United States Patent [19]
Hasegawa

[11] Patent Number: 4,518,695
[45] Date of Patent: May 21, 1985

[54] PROCESS FOR ELUTING EGG WHITE LYSOZYME

[75] Inventor: Mineo Hasegawa, Hachioji, Japan

[73] Assignee: Kewpie Kabushiki Kaisha, Tokyo, Japan

[21] Appl. No.: 443,956

[22] Filed: Nov. 23, 1982

[30] Foreign Application Priority Data

May 29, 1982 [JP] Japan ................... 57-91879

[51] Int. Cl.³ ............................................. C12N 9/36
[52] U.S. Cl. ..................................... 435/206; 435/815
[58] Field of Search ......................................... 435/206

[56] References Cited

U.S. PATENT DOCUMENTS 2,579,455 12/1951 Alderton et al. .................. 435/206
3,515,643 6/1970 Ghielmetti et al. ................. 435/206
4,104,125 8/1978 Takechi et al. .

OTHER PUBLICATIONS

Hackh's Chemical Dictionary, 4th Edition, 1969, p. 239.

Primary Examiner—Lionel M. Shapiro
Attorney, Agent, or Firm—Oblon, Fisher, Spivak, McClelland & Maier

[57] ABSTRACT

In the process of eluting egg white lysozyme by contacting a weakly acidic cation exchange resin having egg white lysozyme adsorbed thereon with an eluting agent comprising a salt solution, an alkali agent is added to the eluate containing the weakly acidic cation exchange resin having egg white lysozyme adsorbed thereon whereby the egg white lysozyme can be eluted more effectively. From the eluate thus obtained, lysozyme can be collected in a high yield by an ordinary collecting method such as salting out.

11 Claims, No Drawings

PROCESS FOR ELUTING EGG WHITE LYSOZYME

BACKGROUND OF THE INVENTION

1. Field of the Invention

The present invention relates to a process for eluting egg white lysozyme from a weakly acidic cation exchange resin having egg white lysozyme adsorbed thereon.

2. Description of the Prior Art

As one process for extracting from egg white lysozyme which is known as a bacteriolytic enzyme present in the egg white in trace amounts, it has previously been proposed to cause a weakly acidic cation exchange resin such as Amberlite, Duolite or Diaion to adsorb the lysozyme and then to elute the lysozyme therefrom. Ordinarily, the lysozyme is eluted from the resin by a method which involves first packing the resin having the lysozyme adsorbed thereon in a column, and thereafter eluting the lysozyme with a salt solution having a pH substantially in the neutral range, e.g., of the order of 6.5 to 7.5, such as an aqueous solution of sodium chloride or ammonium secondary phosphate as is disclosed, for example, in Japanese Patent Pub. No. 7828/1966. The salt solution includes, in addition to a solution obtained by simply dissolving a salt in water, a so-called buffer solution obtained by admixing a salt with an acid or an alkali having either one of the ions constituting the salt (anion or cation).

However, the column method, while ensuring process efficiency due to a continuous operation system, cannot effectively promote intimate contact between the resin having lysozyme adsorbed thereon and the salt solution and thus is unsuitable especially in the case where the resin to be treated is in only a small quantity. For this reason, a batch process is preferred in order to elute lysozyme effectively from a resin having lysozyme adsorbed thereon.

However, when a salt solution of a pH value near the neutral range is actually used in a similar manner for eluting lysozyme from a resin by a batch process in accordance with the elution process described above, it is difficult, even when the elution operation is repeated several times and the lysozyme is collected from each of the eluates thus obtained by a step such as salting out, to increase the recovery, i.e., the yield, in spite of the troublesome elution operation repeated several times. Presumably this is because the concentration of the lysozyme in the eluate has become lower. A solution for this problem has long been sought, but has not been found to date.

As a result of our extensive research, it has been found that, in the above described batch process for eluting egg white lysozyme adsorbed on a resin by contacting the resin with a salt solution, the lysozyme can be eluted more effectively by adding an alkali agent to the eluate containing the resin having lysozyme adsorbed thereon.

SUMMARY OF THE INVENTION

An object of the present invention is to provide a process for eluting egg white lysozyme adsorbed on a weakly acidic cation exchange resin effectively in a high yield on the basis of the findings mentioned above.

The present invention which has achieved this object provides a process for eluting egg white lysozyme by contacting a weakly acidic cation exchange resin having egg white lysozyme adsorbed thereon with an eluting agent comprising a salt solution, which process comprises adding an alkali agent to the eluate containing the weakly acidic cation exchange resin having egg white lysozyme adsorbed thereon.

DETAILED DESCRIPTION OF THE INVENTION

In the process of the present invention, the step of causing the weakly acidic cation exchange resin to adsorb egg white lysozyme may be accomplished in the same manner as the conventional adsorption step of this type. For instance, to a thoroughly homogenized egg white solution having a pH adjusted to fall substantially in the neutral range (ca. 6.5 to 7.5) with addition of acid, is added a weakly acidic cation exchange resin in a quantity of about 20 to 30% by volume of the egg white solution, and the mixture is stirred slowly for several hours (ca. 1 to 8 hours), causing the cation exchange resin to adsorb the lysozyme in the egg white. Ordinarily, the resulting resin is then thoroughly washed with water to obtain a resin having lysozyme adsorbed thereon. The weakly acidic cation exchange resins which can be used herein are commercially available resins such as, for example:

Amberlite IRC-50, Amberlite IRC-84, and Amberlite CG-50, supplied by Rohm & Haas Co.;

Duolite CS-101, Duolite CC-3, and Duolite ES-80, supplied by Diamond Shamrock Chemial Co.;

Dowex CCR-2, supplied by the Dow Chemical Co.;

Lebatit CNP and Lebatit CNP-80, supplied by Bayer Co.; and

Diaion WK-10, Diaion WK-20, and Diaion WK-11, supplied by Mitsubishi Kasei Kogyo K.K., Japan.

The weakly acidic cation exchange resin, when actually used, is advantageously converted by treatment with caustic soda or other alkalis into a resin substituted with about 1.2 to 1.4 meq./ml resin of a cation except for $H^+$, such as $Na^+$, $K^+$ and $NH_4^+$, prior to the addition to the egg white solution since the pH of the egg white solution which has been adjusted to neutrality does not appreciably vary when the cation substituted resin is added thereto.

Lysozyme is eluted from the resin thus obtained.

The salt solution used for the elution of lysozyme may be any of conventional salt solutions, such as, for example, an aqueous solution of sodium, potassium and ammonium salts, more specifically, an aqueous solution of sodium chloride, potassium chloride, sodium sulfate and ammonium secondary phosphate having a pH in the vicinity of neutrality, or a buffer solution obtained by admixing any of these salts with an aqueous solution of an acid or an alkali having either one of the ions (anion or cation) constituting the salt.

The salt solution is used ordinarily at a concentration of about 0.3M or higher so that the lysozyme adsorbed on the resin can be easily eluted from the resin. It is preferable from the viewpoint of ease in handling that the elution operation be carried out at a salt solution: resin ratio of 100:10 to 100 parts by volume.

The unique feature of the present invention, which relates to a process for eluting lysozyme by contacting a weakly acidic cation exchange resin having egg white lysozyme adsorbed thereon with an eluting agent comprising a salt solution, is the addition of an alkali agent to the eluate containing the resin.

The alkali agent to be added must be one having a strong alkalinity such that the pH of its aqueous solution of 1 mole concentration is 13 or higher, such as caustic soda or caustic potash, and is preferably used in the form of an aqueous solution of a concentration of the order of 0.1N to 2N. If a solution of lower concentration of the alkali agent is added to the eluate, the overall quantity of the resultant solution mixture will be increased, while a solution of higher concentration tends to result in denaturation of lysozyme.

The quantity of the alkali agent to be added may be of an order such that the pH of the eluate can be maintained in the neutral range, i.e., about 6.5 to 8.0. In the case where this quantity is so small that the pH of the eluate becomes lower than 6.5, lysozyme cannot easily be eluted from the resin. Conversely, the addition of the alkali agent in an excessive quantity such as to make the pH of the eluate higher than 8.0 tends to result in partial denaturation of lysozyme.

The rate at which the alkali agent is added depends on the state in which lysozyme is adsorbed on the resin and thus cannot be determined definitively. Generally speaking, the alkali agent may be added in a 1N solution at a rate of about 0.5 to 7 ml/min., preferably about 3 to 4 ml/min., per liter of the resin; in a 0.5N solution at a rate of about 1 to 14 ml/min., preferably about 6 to 8 ml/min.; and in a 2N solution at a rate of about 0.3 to 4 ml, preferably about 2 to 3 ml/min., with stirring for about 5 to 30 minutes.

In order to prevent a rapid local change of the pH of the eluate and to ensure uniform pH throughout the eluate, it is desirable that the alkali agent be added while the eluate is stirred at a speed, for example, of 30 r.p.m. The addition of the alkali agent and stirring of the eluate may be conducted intermittently provided that the pH of the eluate is maintained under the conditions specified hereinbefore, but continuous addition and stirring is preferred in order to maintain constant pH conditions.

By adding the alkali agent to the eluate in the process of eluting lysozyme from the resin, lysozyme adsorbed on the resin can be eluted effectively in a high yield as will be apparent from the Example of Experiment described hereinlater. Presumably, this is because the addition of the alkali agent prevents the lowering of the pH of the eluate caused by the substitution of lysozyme for a salt (ion exchange), thereby promoting the elution of the lysozyme.

The effectiveness of the solution process of the present invention in eluting lysozyme and hence in improving the yield of extraction of lysozyme from egg white will now be shown by the following Example of Experiment in which lysozyme was actually eluted and then collected.

EXAMPLE OF EXPERIMENT

A. Preparation of Resin Having Lysozyme Adsorbed Thereon

To 1,000 ml of a thoroughly homogenized egg white solution having a pH adjusted to 6.5 with addition of hydrochloric acid was added 200 ml of a cation exchange resin (Dowex CCR-2) which had been converted by alkali treatment into a resin substituted with 1.3 meq./ml resin of $Na^+$, and the resulting mixture was stirred slowly for 300 minutes. The egg white solution was then removed by decantation and filtration and the residue was washed three times with 800 ml of pure water to obtain a resin having lysozyme adsorbed thereon.

B. Elution of Lysozyme

To about 200 ml of the resin obtained in the manner described above was added 800 ml of a 3% aqueous sodium chloride solution. To this mixture was further added a 1N NaOH solution at a rate of about 0.6 ml/min. over a period of 10 minutes with stirring at a speed of 30 r.p.m. to maintain the pH of the eluate at about 7.0 and to elute the lysozyme into the salt solution.

C. Collection of Eluted Lysozyme

The solution containing the resin was then filtered through a filter cloth of 80 mesh, and the pH of the filtrate thus obtained was adjusted to 9.5 with addition of 0.5N NaOH solution. To this filtrate was added sodium chloride until the sodium chloride concentration thereof reached 5%, and lysozyme was collected by the salting out method. The quantity of the lysozyme thus collected was 9.2 g in cake form which was found, on conventional potency analysis, to correspond to 3.1 g of pure crystalline lysozyme.

As a control, the following elution process was conducted. To about 200 ml of the resin with lysozyme adsorbed thereon prepared in accordance with the procedure A described above, was added 800 ml of a 0.5M sodium phosphate buffer solution (pH 7.0) containing 3% of sodium chloride, and the mixture was stirred for 10 minutes at a speed of 30 r.p.m. to elute the lysozyme into the salt solution. This resin containing solution was filtered through a filter cloth of 80 mesh, and lysozyme was collected from the filtrate thus obtained under the same conditions as in the procedure C. In this case, the filtered resin was further subjected to elution and collection three times, respectively, whereupon lysozyme was collected in the following quantities.

|  | Lysozyme in cake form (g) | Pure crystalline lysozyme (g) on potency analysis |
| --- | --- | --- |
| 1st time | 4.5 | 1.5 |
| 2nd time | 1.1 | 0.3 |
| 3rd time | 0.5 | 0.1 |
| 4th time | not precipitated | 0.0 |
| Total | 6.1 | 1.9 |

It will be noted from the results obtained in the above Example of Experiment that, in the process of eluting with a salt solution lysozyme from a resin having lysozyme adsorbed thereon, the lysozyme can be eluted in higher yields by the process of the present invention in which a salt solution is employed and also an alkali agent is added than by a conventional process in which a salt solution having a pH substantially in the neutral range is utilized.

In order to indicate more fully the nature and utility of this invention, the following specific examples of practice constituting preferred embodiments of the invention are set forth, it being understood that these examples are presented as illustrative only and are not intended to limit the scope of the invention.

EXAMPLES

Example 1

A resin having lysozyme adsorbed thereon was prepared as in the Example of Experiment described above except that Na-form Dowex CCR-2 was replaced by the same quantity of Amberlite IRC-50 which had been converted by alkali treatment into a resin substituted with 1.2 meg./ml resin of $K^+$. The resin obtained was then subjected to elution and collection in accordance with the procedures B and C of the Example of Experiment, whereupon 8.9 g of lysozyme was collected in cake form which was found, on potency analysis, to correspond to 2.9 g of pure crystalline lysozyme. The pH of the eluate was maintained at about 7.5 throughout the elution process.

Example 2

Lysozyme was eluted by the procedure B of the Example of Experiment except that the 3% aqueous sodium chloride solution used as a salt solution and the 1N NaOH solution were replaced respectively by a 3% aqueous potassium chloride solution and a 1N KOH solution. The eluate thus obtained was subsequently treated by the procedure C of the Example of Experiment, whereupon 8.7 g of lysozyme was collected in cake form which was found, on potency analysis, to correspond to 2.8 g of pure crystalline lysozyme. The pH of the eluate was maintained at about 6.7 throughout the elution process.

Example 3

Lysozyme was collected under the same conditions as in the Example of Experiment except that lysozyme was eluted into a salt solution containing a resin to which was added a 1N NaOH solution at a rate of about 0.8 ml/min. over a period of 10 minutes with stirring at a speed of 40 r.p.m. The quantity of the lysozyme thus collected was 9.0 g in cake form which was found, on potency analysis, to correspond to 3.0 g of pure crystalline lysozyme. The pH of the eluate was maintained at about 7.3 throughout the elution process.

Example 4

A resin having lysozyme adsorbed thereon was prepared as in the Example of Experiment except that Na-form Dowex CCR-2 was replaced by the same quantity of Diaion WK-10 which had been converted by alkali treatment into a resin substituted with 1.2 meq./ml resin of $K^+$. The resin obtained was then subjected to elution and collection in accordance with the procedures B and C of the Example of Experiment, whereupon 9.2 g of lysozyme was collected in cake form which was found, on potency analysis, to correspond to 3.0 g of pure crystalline lysozyme. The pH of the eluate was maintained at about 7.4 throughout the elution process.

Example 5

Lysozyme was eluted into a salt solution by the procedure B of the Example of Experiment except that the 3% aqueous sodium chloride solution used as a salt solution was replaced by a 0.5M sodium phosphate buffer solution containing 3% of sodium chloride and having a pH of 7.0. The eluate obtained was then treated by the procedure C of the Example of Experiment, whereupon 9.1 g of lysozyme was collected in cake form which was found, on potency analysis, to correspond to 2.9 g of pure crystalline lysozyme. The pH of the eluate was maintained at about 7.0 throughout the elution process.

What I claim is:

1. In a process for eluting egg white lysozyme by contacting a weakly acidic cation exchange resin having egg white lysozyme adsorbed thereon with an eluting agent comprising a salt solution having a pH of about 6.5 to 8.0, the improvement wherein an alkali agent is added to the mixture of the weakly acidic cation exchange resin having egg white lysozyme adsorbed thereon and the eluting agent in a quantity such that the pH of the mixture during elution is between about 6.5 and 8.0.

2. The process according to claim 1 wherein the alkali agent has a strong alkalinity such that the pH of its aqueous solution of 1 mole concentration is 13 or higher.

3. The process according to claim 2 wherein the alkali agent is selected from the group consisting of caustic soda and caustic potash.

4. The process according to claim 1 wherein the alkali agent is used in a 0.1N to 2N aqueous solution.

5. The process according to claim 1 wherein the alkali agent is added in a 1N solution at a rate of about 0.5 to 7 ml/min. per liter of the resin having lysozyme adsorbed thereon over a period of about 5 to 30 minutes while the mixture is stirred.

6. The process according to claim 1 wherein the alkali agent is added in a 0.5N solution at a rate of about 1 to 14 ml/min. per liter of the resin having lysozyme adsorbed thereon over a period of about 5 to 30 minutes while the mixture is stirred.

7. The process according to claim 1 wherein the alkali agent is added in a 2N solution at a rate of about 0.3 to 4 ml/min. per liter of the resin having lysozyme adsorbed thereon over a period of about 5 to 30 minutes while the mixture is stirred.

8. The process according to claim 1 wherein the alkali agent is added while the mixture is stirred.

9. The process according to claim 1 wherein the weakly acidic cation exchange resin has been converted by alkali treatment into a resin of the cation substituted form, the cation being $Na^+$, $K^+$, $NH_4^+$, and/or the like, exclusive of $H^+$ prior to the adsorption of the egg white lysozyme.

10. The process according to claim 1 wherein the salt solution is an aqueous solution of any of the salts selected from the group consisting of sodium potassium and ammonium salts.

11. The process according to claim 1 wherein the salt solution is a buffer solution obtained by admixing any of the salts selected from the group consisting of sodium, potassium and ammonium salts with an aqueous solution of an acid or an alkali having either one of the ions constituting the salt, i.e., anion or cation.

* * * * *